United States Patent
Watanabe (10) Patent No.: US 8,146,532 B2
(45) Date of Patent: Apr. 3, 2012

(54) AUTOMATIC MILKING APPARATUS FOR LABORATORY ANIMALS

(75) Inventor: Toshi Watanabe, Tokyo (JP)

(73) Assignee: Nihon University, Tokyo (JP)

( * ) Notice: Subject to any disclaimer, the term of this patent is extended or adjusted under 35 U.S.C. 154(b) by 813 days.

(21) Appl. No.: 12/293,070

(22) PCT Filed: Feb. 7, 2007

(86) PCT No.: PCT/JP2007/052082
§ 371 (c)(1),
(2), (4) Date: Sep. 15, 2008

(87) PCT Pub. No.: WO2007/108241
PCT Pub. Date: Sep. 27, 2007

(65) Prior Publication Data
US 2009/0078206 A1    Mar. 26, 2009

(30) Foreign Application Priority Data
Mar. 16, 2006 (JP) ................................. 2006-073264

(51) Int. Cl.
*A01J 5/00* (2006.01)
(52) U.S. Cl. ................ 119/14.47; 119/14.1; 119/14.17; 119/14.18; 119/14.41
(58) Field of Classification Search ............... 119/14.1, 119/14.17, 14.18, 14.47, 14.41
See application file for complete search history.

(56) References Cited

U.S. PATENT DOCUMENTS

| 3,556,053 | A | * | 1/1971 | Padman et al. | 119/14.08 |
| 3,938,470 | A | * | 2/1976 | Pace | 119/14.1 |
| 4,114,847 | A | * | 9/1978 | Bogensberger | 248/104 |
| RE36,883 | E | * | 9/2000 | Krenzel | 362/191 |

(Continued)

FOREIGN PATENT DOCUMENTS

| WO | 98/51144 A1 | 11/1998 |
| WO | 01/45498 A1 | 6/2001 |
| WO | 01/67064 A1 | 9/2001 |
| WO | 2005/041646 A1 | 5/2005 |

OTHER PUBLICATIONS

"Breast Milk Can Now be Collected From Living Small Experimental Animals"; The Nikkan Kogyo Shinbun, Ltd.; Oct. 31, 2002; p. 20.

*Primary Examiner* — Joshua J Michener
*Assistant Examiner* — Justin Benedik
(74) *Attorney, Agent, or Firm* — Sughrue Mion, PLLC (57) ABSTRACT

An automatic milking apparatus for laboratory animals that can facilitate and stabilize the positioning of a teat cup 20 is provided for full automation of a milking operation. An end of a first milk tube 12 attached to a teat cup 20 for laboratory animals is attached to a free end of a flexible arm A having one end fixed to a suitable base (milk collecting container stand B). The flexible arm A includes a laminated body 40 including a long member 41 formed of a material that is flexible and after being flexed, can maintain the shape (for example, a lead plate) and a steel plate member 42, the laminated body 40 being coated by a coating member 50, the members being in contact with each other in such a manner that they slip relative to each other upon being flexed in their entirety, the flexible arm A including a secured part 53 formed at the one end, the secured part 53 preventing relative movement of the respective members. The tip of the flexible arm A is not displaced after being positioned.

16 Claims, 6 Drawing Sheets

U.S. PATENT DOCUMENTS

| | | |
|---|---|---|
| 6,289,845 B1 | 9/2001 | Andersson |
| 6,308,656 B1 | 10/2001 | Milbrath et al. |
| 6,382,130 B1 * | 5/2002 | Rooney ................. 119/14.04 |
| 6,532,893 B1 * | 3/2003 | Edholm ................. 119/14.47 |
| 6,814,028 B2 * | 11/2004 | Watanabe ................. 119/14.44 |
| 6,981,466 B2 * | 1/2006 | Lindholm ................. 119/14.02 |
| 2003/0051668 A1 | 3/2003 | Watanabe |
| 2004/0133151 A1 * | 7/2004 | Watanabe ................. 604/74 |

* cited by examiner

AUTOMATIC MILKING APPARATUS FOR LABORATORY ANIMALS

CROSS REFERENCE TO RELATED APPLICATIONS

This application is a National Stage of International Application No. PCT/JP 2007/052082 filed Feb. 7, 2007, claiming priority based on Japanese Patent Application No. 2006-073264 filed Mar. 16, 2006, the contents of all of which are incorporated herein by reference in their entirety.

TECHNICAL FIELD

The present invention relates to a milking apparatus for laboratory animals, specifically, an automatic milking apparatus suitable for relatively small and prolific laboratory animals such as rats and mice.

BACKGROUND ART

In recent years, substances toxic to living bodies, such as environmental pollutants, carcinogenic substances, and endocrine disruptive (chemical) substances, are posing a significant global issue. There are concerns that these toxic substances may affect living bodies through breast milk or commercially sold milk. The influence these extrinsic toxic substances may have on living bodies could be clarified if it becomes possible to collect milk from laboratory animals, such as rats or mice, in a simpler way.

However, because relatively small and prolific laboratory animals such as rats and mice have small teats and produce only small amounts of milk, no effective milking apparatuses for these animals have been proposed. For example, it is difficult to obtain the milk of rats directly from their teats, and, therefore, in locations such as laboratories, the milk is normally collected from the stomach of a newborn rat that has been fed. The milk collected from the stomach, however, could have had its milk components broken down or digested through mixing or stirring with saliva and gastric fluid, and it is questionable if such milk could be considered true milk.

In response to these needs, the present inventor had already developed an improved milking apparatus capable of milking directly from the udder of a rat or a mouse, and a teat cup therefor, and had filed an application therefor (Patent Document 1 and Patent Document 2). This milking apparatus enables even a single experimenter to perform a milking operation on a laboratory animal, thereby allowing for the acquisition of universal milking data that is not subject to individual differences between experimenters.

Patent Document 1: Domestic Re-publication of PCT International Publication ("kohyo") WO 01/067064

Patent Document 2: JP Patent Publication (Kokai) No. 2005-130774 A

DISCLOSURE OF THE INVENTION

The present inventor and others milked rats, mice, and beagle dogs for experiment purposes and miniature pigs many times using the above-described milking apparatus and teat cup, and obtained good results. However, when a laboratory animal such a rat or a mouse under anesthesia is milked, it is difficult to conduct milking with a teat cup accurately secured to the position of a teat of the mother, and the experimenter needs to hold on to the rat, mouse or the like with one hand and continuously fit the teat cup on the mother's teat with the other hand, or turning it upward and continuously fitting the teat cup on the teat with both hands. Consequently, where it becomes necessary to introduce inhalation anesthesia during milking, for example, he/she experienced the necessity to temporarily stop milking. For that reason, it has been difficult to fully automate milking. Also, when there arises the need to observe or measure the milked amount at all times during milking, it has been difficult to response to such need.

The present invention has been made in view of the aforementioned circumstances, and an object of the present invention is to provide an automatic milking apparatus for laboratory animals which is a milking apparatus for laboratory animals having the structure described in Patent Document 1 or Patent Document 2 in which after positioning and fixing a teat cup on a teat of a laboratory animal, milking can be continued automatically without giving trouble to experimenters. Also, another object of the present invention is to provide an automatic milking apparatus for laboratory animals configured to enable observing or measuring an amount of milk at all times during automatic milking.

The aforementioned objects can be achieved by providing a milking apparatus for laboratory animals having the structure described in Patent Document 1 or Patent Document 2 in which: a teat cup, which is attached to a tip of a milk tube, is attached to a tip of a flexible arm; and the tip of the flexible arm can freely is moved in a three-dimensional space via an experimenter's manual operation, and once positioned, it can remain at the position (i.e., not displaced) even though the experimenter releases his/her hands from it.

The present inventor has conducted many experiments to obtain a flexible arm suited to such objects, using existing flexible arms, but could not find a flexible arm that provides both easy handling and the property of no displacement occurring when it is released from force at a predetermined position.

In other words, although there is a multijoint flexible arm as one flexible arm type, a multijoint flexible arm has a complicated structure and in addition, each joint has a mechanical structure, resulting in incompatibility of easy movement and a position-holding feature, and where easy movement is prioritized, it becomes difficult to hold the tip at a relevant position without displacement after moving the tip to that position. In order to prevent displacement, separate means for securing the joints after the movement is required. For the aforementioned reasons, use of a multijoint flexible arm was not proper as a teat cup positioning means in a milking apparatus for laboratory animals.

A flexible arm having a structure formed by joining multiple cylindrical bodies, which is used in a desk lamp, does not provide easy handling and causes a considerable degree of displacement after positioning, which was also not proper as a teat cup positioning means in a milking apparatus for laboratory animals.

Therefore, an experiment was conducted using a flexible ruler-shaped arm having a high degree of freedom in movement and providing easy handling. The flexible arm used in the experiment is one formed by inserting a laminated body of long members formed of a material that is flexible and after being flexed, can maintain the shape (for example, a long lead plate) and steel plate members arranged along the long members, into a coating material made of resin, and both ends thereof are open. A flexible arm having this structure provides easy handling and free movement, but the tip is displaced in a short period of time upon releasing the arm from the handling weight by releasing the hands from it after movement.

Therefore, the present inventor conducted an experiment in which an industrial adhesive is embedded in one end of a flexible arm to integrally secure lead plate members, steel plate members and a coating material so that no relative movement occurs between each of them, the secured side is fixed to a base, and a teat cup is attached to another end which is open, as a trial. As a result, positioning was easy, and even though the hands were released from the arm after positioning, the teat cup remained at its original position over a long period of time without causing displacement.

In other words, the present inventor realized that milking can be continued automatically without giving trouble to an experimenter by attaching a teat cup to a tip of a flexible arm having the aforementioned structure since the arm enables easy positioning and securing of the teat cup to a teat of a laboratory animal and the teat cup remains at that position even though the experimenter releases his/her hands from it.

The present invention has been made based on the above findings, and an automatic milking apparatus for laboratory animals according to the present invention provides an automatic milking apparatus for laboratory animals in which an end of a milk tube having another end connected to a teat cup for laboratory animals to be fitted onto a udder of a laboratory animal is connected to a negative-pressure generating source via a milk collecting container to collect milk from the laboratory animal into the milk collecting container through suction pulsation provided by the negative-pressure generating source, characterized in that the end of the milk tube connected to the teat cup for laboratory animals is supported by a free end of a flexible arm with one end fixed to a suitable base, the flexible arm including a laminated body that includes a long member formed of a material that is flexible and after being flexed, can maintain the shape and a steel plate member arranged along the long member, the laminated body being coated by a coating member, the members being in contact with each other in such a manner that they slip relative to each other upon being flexed in their entirety, the flexible arm including a secured part formed at the one end, the secured part preventing relative movement of the respective members.

For the milking apparatus for laboratory animals and the teat cup required in the present invention, those described in Patent Document 1 and Patent Document 2 previously proposed by the present inventor can be used as they are. Also, the milking procedure as described in them may be applied.

The automatic milking apparatus for laboratory animals according to the present invention uses a flexible arm having the above-described special structure, providing ease and reliability in positioning a teat cup and securing it to that position. Accordingly, it becomes unnecessary for an experimenter to continue to fit the teat cup on a mother's teat by his/her hands during milking once he/she accurately secure the teat cup to the teat position of the laboratory animal. In other words, an experimenter can leave the milking apparatus during milking, enabling automatic operation of the milking apparatus. Where necessary, it is possible to perform work such as introduction of inhalation anesthesia to the laboratory animal totally separately from the apparatus operation, without interrupting milking performed by the milking apparatus, enabling easy introduction of inhalation anesthesia as well as avoiding accidents due to inhalation anesthesia.

In another structure of an automatic milking apparatus for laboratory animals according to the present invention, a milk tube holder that can slidably support the milk tube is attached to the free end of the flexible arm, and the milk tube is supported by the free end of the flexible arm via the milk tube holder.

In the automatic milking apparatus having this structure, the up-and-down position of the teat cup attached to the milk tube tip can be changed merely by sliding the milk tube along the milk tube holder without moving the flexible arm itself, and accordingly, it is possible to make the teat cup position more easily follow changes in teat position according to the individual differences in laboratory animals to be milked.

Still another structure of an automatic milking apparatus for laboratory animals according to the present invention is characterized in that: the automatic milking apparatus for laboratory animals further comprises a milk collecting container stand that is a transparent cylindrical body; a vertical hole to hold the milk collecting container is formed in the milk collecting container stand; a scale for measuring an amount of milk in the milk collecting container is provided on an inner surface of the vertical hole; and the secured part of the flexible arm is fixed to the milk collecting container stand.

In the automatic milking apparatus having this structure, the milk collecting container stand functions also as a magnifying glass, making it possible to observe the milked amount at all times during automatic milking and reliably measure the milked amount, for example, with the experimenter's eyes.

In the flexible arm used in the automatic milking apparatus for laboratory animals according to the present invention, the secured part of the flexible arm can be formed by any means if it hinders relative movement of the respective members, and examples of the means can include securing via pasting using an adhesive, and fastening by means of inserting and then squashing locking pins.

In the flexible arm used in the automatic milking apparatus for laboratory animals according to the present invention, examples of the "long member formed of a material that is flexible and after being flexed, can maintain the shape" can include an aluminum plate, a lead plate and a resin plate. Specific examples of the resin plate include a long resin material formed by stretching a polyethylene resin in a signal axis direction and controlling the molecular arrangement (for example, product name "Forte" manufactured by Sekisui Chemical Co., Ltd.). Among these, a material that can maintain its curved shape without substantial change even though releasing the hands from it after it is flexed (curved) with a curvature radius in a predetermined range, that is, a material having a resilience that is close to zero or extremely small is preferable, and use of such material together with a steel plate member, which is a proper string steel having a large resilience, provides necessary flexibility to the flexible arm. In the experiments conducted by the present inventor, an aluminum plate was most suitable for the long member.

The steel plate member gives load bearing to the flexible arm by means of the elasticity the steel plate has, and a steel plate member (spring steel) having proper cross-sectional dimensions is selected through experiments in consideration of weight imposed on the free end of the flexible arm during use. As a result, necessary elasticity and recoverability are provided to the flexible arm. The coating member ensures the adhesion between the respective members, and fixes up the appearance of the flexible arm. Here, the "recoverability" does not means resilience (i.e., returning to the original shape by means of elasticity when released from an external force), but easiness of returning the flexible arm to the original shape by means of giving an external force thereto.

The cross-sectional dimensions of the long member and the steel plate member included in the flexible arm are suitably determined according to the weight of the teat cup to be attached to the flexible arm. At least, it is necessary for a flexible arm to have a flexural strength enough to resist natural deformation due to the weight of the teat cup. Where the steel plate member is overly thick, the flexible arm will have resilience, resulting in impossibility to perform positioning, and accordingly, one having a thickness in the range that does not cause resilience is selected and used. Ordinarily, one having a thickness of 0.2 to 0.5 mm is used.

Desirably, the coating member is of a material having flexibility and toughness with no influence on the flexibility of the flexible arm, and it is desirably of a synthetic resin material such as flexible vinyl chloride. Among them, a silicon resin material is preferable. When there is a gap between the laminated body and the coating member, a gap also occurs between the lead member and the steel plate member, reducing the frictional force between the respective members, resulting in the free end easily performing a positional change (displacement) after positioning, and accordingly, a coating member having an inner diameter that does not cause such gap is selected. The outer shape of the coating member can arbitrarily be determined: it is not limited to a shape following the outer shape of the laminated body, and a square shape, a circular shape, etc., may be selected depending on the intended use.

There are no limitations on the laminate structure of the laminated body. Examples of the laminated structure can include: one long member and two steel plate members (one steel plate member laminated to each of the outer sides of one long member); two long members and three to four steel plate members (one or two steel plate members laminated between two long members and one steel plate member laminated to each of the outer sides of the long members); and three long members and four to six steel plate members (one or two steel plate members are laminated between each of three long members and one steel plate member is laminated to each of the outer sides of the long members).

The flexible arm used in the automatic milking apparatus for laboratory animals according to the present invention may have a resin sheet interposed between the respective members as necessary. As a result, good slippage will be provided between the respective layers, making positioning easy. However, when the slippage between the layers is overly good, the resilience of the steel plate member prevails, which may result in displacement easily occurring after position setting. In such a case, no resin sheet is interposed.

Use of the automatic milking apparatus for laboratory animals according to the present invention enables automatically collect milk directly from the udder of a laboratory animal such as a rat or a mouse. Consequently, work such as introduction of inhalation anesthesia to the laboratory animal can be performed entirely separately from the apparatus operation, without interrupting milking performed by the milking apparatus. Also, a preferred embodiment of an automatic milking apparatus for laboratory animals according to the present invention makes it possible to observe and measure the milked amount at all times during automatic milking.

BRIEF DESCRIPTION OF THE DRAWINGS

Hereinafter, an embodiment of an automatic milking apparatus for laboratory animals according to the present invention will be described with reference to the drawings.

In FIG. 4, FIG. 4a is an overall perspective view of a structure of a flexible arm used in an automatic milking apparatus for laboratory animals according to the present invention, FIG. 4b is a cross-sectional view taken along line b-b of FIG. 4a, and FIG. 4c is a front view.

DESCRIPTION OF SYMBOLS

B . . . milk collecting container stand as base, 2 . . . vertical hole, 3 . . . scale, 10 . . . milk collecting container, 11 . . . sealing cap, 12 . . . first milk tube, 13 . . . second milk tube, 20 . . . teat cup, 31 . . . backflow prevention valve, 33A . . . electromagnetic valve, 34 . . . negative pressure tank, 35 . . . vacuum pump, A, A1 . . . flexible arm, 40 . . . long laminated body, 41 . . . long member, 42 . . . steel plate member, 50 . . . coating member, 51 . . . inner space of coating member, 52 . . . adhesive, 53 . . . secured part of flexible arm, 54 . . . locking pin, 55 . . . milk tube holder, 56 . . . U-shaped clip.

BEST MODE FOR CARRYING OUT THE INVENTION

Figure 1:
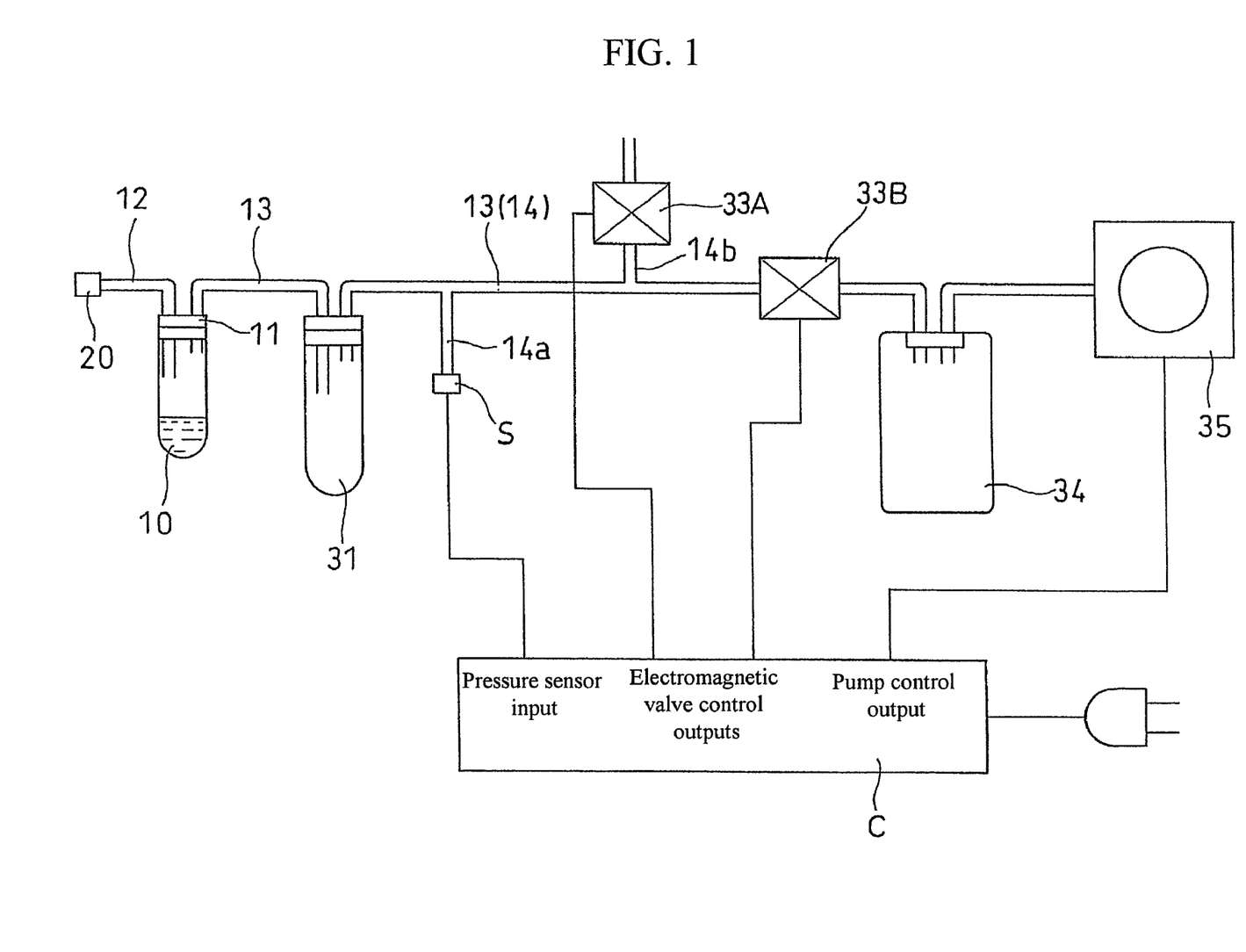
FIG. 1 is a diagram illustrating an overall configuration of an embodiment of an automatic milking apparatus for laboratory animals according to the present invention.
Figure 2:
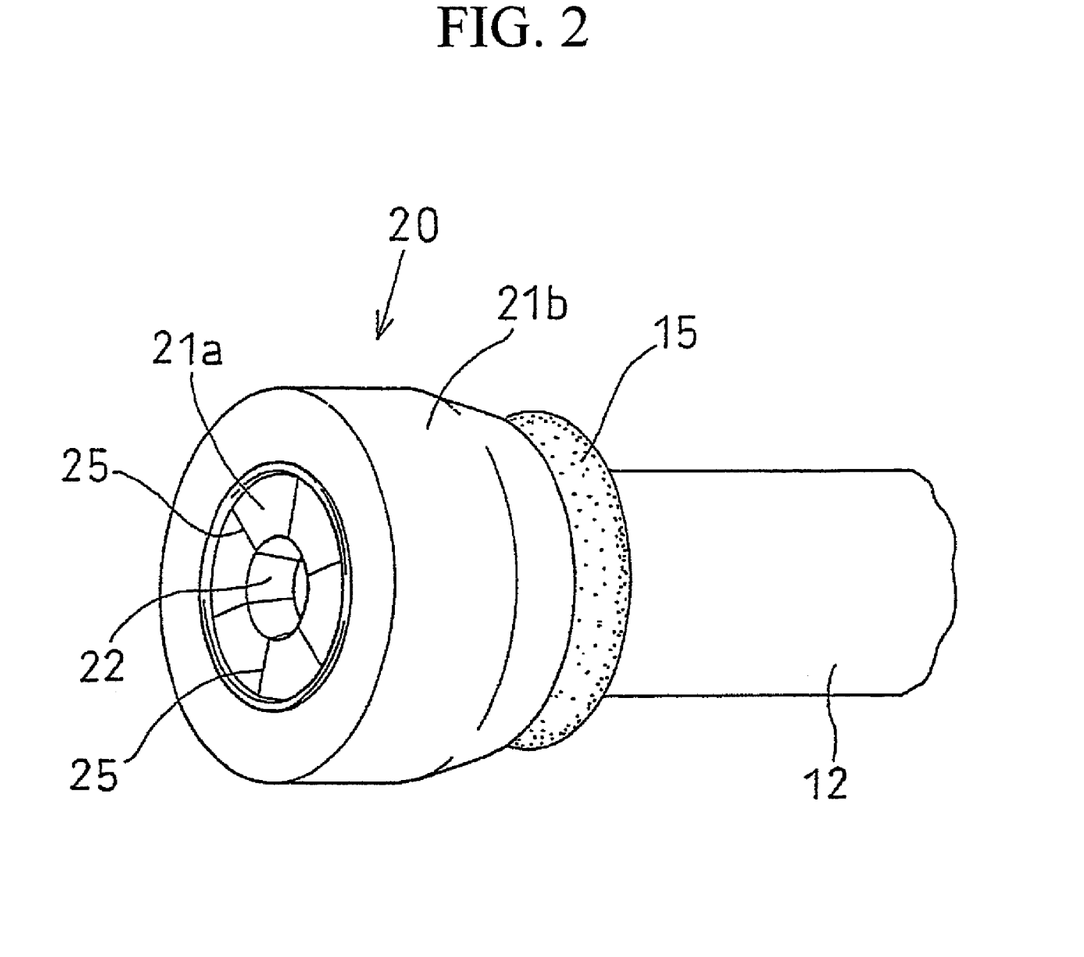
FIG. 2 is a diagram illustrating an example of a teat cup used in the apparatus shown in FIG. 1.
Figure 3:
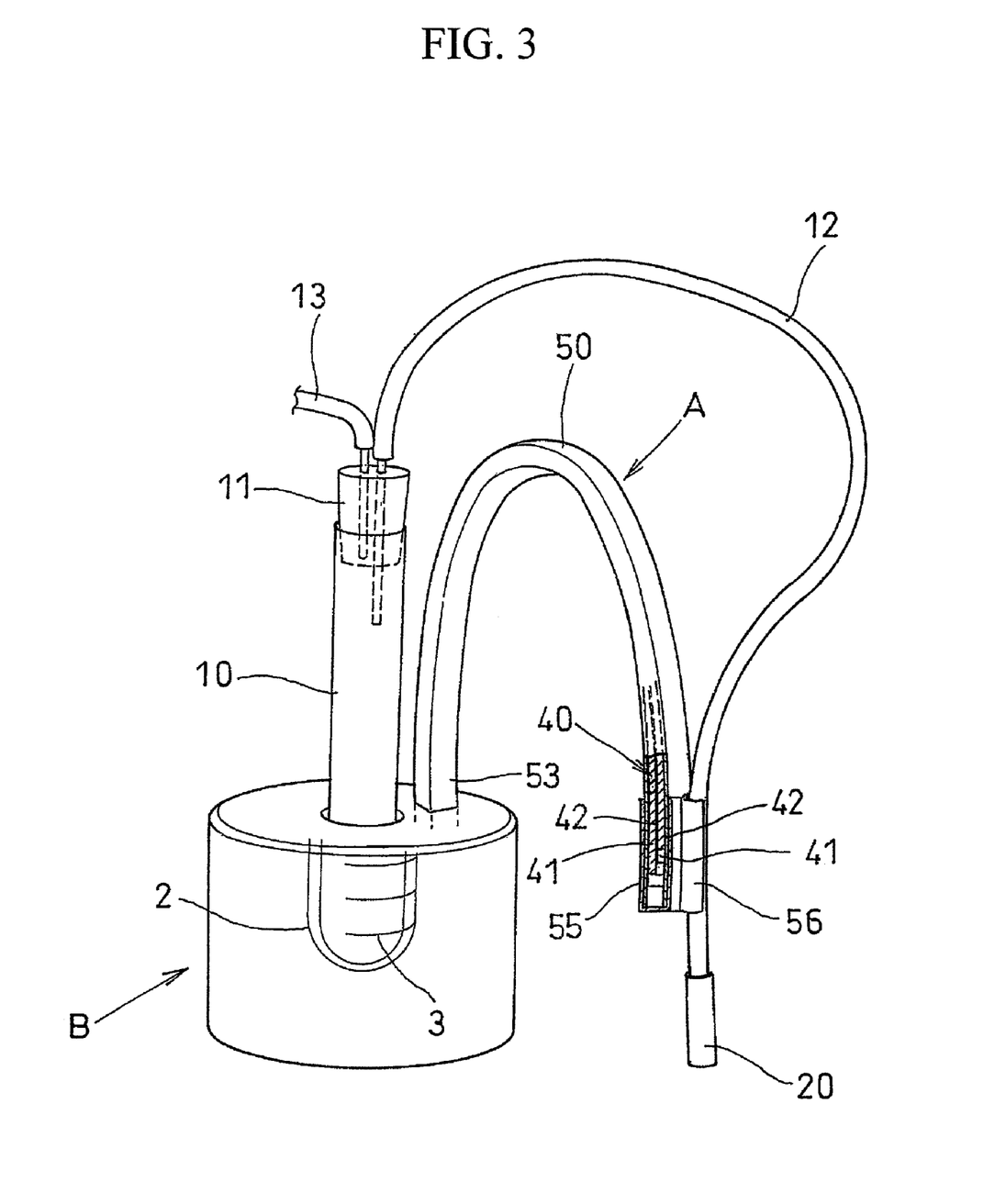
FIG. 3 is a diagram illustrating a teat cup and milk collecting container portion of the apparatus shown in FIG. 1.

In this milking apparatus for laboratory animals, a milk collecting container 10, which is a transparent cylindrical body like a test tube is capped with a sealing cap 11, and one end of each of a first milk tube 12 and a second milk tube 13 is inserted into the sealing cap 11 in such a manner that they are in fluid communication with the milk collecting container 10. On the other end of the first milk tube 12, a teat cup 20, one example of which is shown in FIG. 2, is replaceably mounted, and also, the other end of the second milk tube 13 is connected to a vacuum pump 35 via a backflow prevention valve 31 and a negative pressure tank 34 that functions as an accumulator. As shown in FIG. 3, one end of the teat cup 20 is supported by a free end of a flexible arm A unique to the present invention, one end of which is fixed to a suitable base, and in this example, the base doubles as a milk collecting container stand B for the milk collecting container 10. This point will be described in details later.

The second milk tube 13 includes a first branch tube 14a fitted with a pressure sensor S. The second milk tube 13 further includes a second branch tube 14b on the downstream side, which is fitted with a first bidirectional electromagnetic valve 33A. By opening the first bidirectional electromagnetic valve 33A, the second branch tube 14b can be opened to the atmosphere. Downstream of the second branch tube 14b, the second milk tube 13 is fitted with a second bidirectional electromagnetic valve 33B. By opening the second bidirectional electromagnetic valve 33B, the second milk tube 13 can be placed in fluid communication with the negative pressure tank 34.

A computer C is connected to the pressure sensor S, the first and second electromagnetic valves 33A and 33B, and the vacuum pump 35 such that information can be transmitted among them. The computer C controls the input of pressure information from the pressure sensor S and the outputs for controlling the open/close timing of the first and second electromagnetic valves 33A and 33B, and the operation of the vacuum pump 35, for example.

When milking, the vacuum pump 35 is operated with the first and second electromagnetic valves 33A and 33B closed, to generate a negative pressure in the negative pressure tank 34. When a predetermined pressure is achieved, the second electromagnetic valve 33B is opened, whereby the air in the second milk tube 13 is drawn into the negative pressure tank 34, and changed to have a predetermined negative pressure (set pressure) from the atmospheric pressure. At this point, the second electromagnetic valve 33B is closed, whereby the set negative pressure condition is achieved and maintained in the second milk tube 13, making the teat cup 20 start sucking. After this condition is maintained for a certain period of time, the first electromagnetic valve 33A is opened, whereby the inside of the second milk tube 13 is opened to the atmosphere and the pressure returns to the atmospheric pressure. After this condition is maintained for a certain period of time, the first electromagnetic valve 33A is closed and the second electromagnetic valve 33B is again opened. Thereafter, this cycle is repeated a set number of times, whereby the negative pressure and the atmospheric pressure are alternately provided at the tip of the teat cup 20, and a required milking operation is carried out.

As shown in FIG. 2, in this example, the teat cup 20 is made of soft rubber (e.g., silicon rubber) and formed generally in the shape of a cylinder with an internal diameter of approximately 4 mm, an external diameter of approximately 7 mm, and a height of approximately 4 mm. The tip of the teat cup 20 is closed with a top surface portion (liner) 21a. The top surface portion 21a, which is the liner with which the udder of a mother rat comes into contact, has a thickness b of approximately 0.4 mm. In the center of the liner, there is formed a conically shaped insertion opening 22, into which a rat's teat is inserted, having a diameter of approximately 1.8 mm at the tip and a diameter of approximately 1.5 mm at the rear end.

During the milking period (ultimate vacuum period, or suction period), the insertion opening 22 in the top surface portion (liner) 21a of this teat cup 20 widely opens, allowing milk to be sucked from the teat. The sucked milk is stored in the milk collecting container 10 via the first milk tube 12. During the rest period (ultimate atmospheric pressure period, or atmospheric pressure/massage period, when no negative pressure is present), the insertion opening 22 formed in the top surface portion 21a becomes smaller by its own resilience and closed (i.e., returned back to its original position shown in the solid line in FIG. 2).

The aforementioned automatic milking apparatus for laboratory animals has a configuration that is the same as those of the known milking apparatuses described in Patent Document 1 and Patent Document 2 except the configuration in which the teat cup 20 is supported by the flexible arm A unique to the present invention. Also, the teat cup 20 is a known one. In other words, FIGS. 1 and 2 show an example, and the configuration in which an end of the milk tube 12 having another end connected to the teat cup 20 for laboratory animals to be fitted onto the udder of a laboratory animal is connected to the negative-pressure generating sources 34 and 35 via the milk collecting container 10 to collect milk from the laboratory animal into the milk collecting container 10 through suction pulsation provided by the negative-pressure generating sources, which is required in a milking apparatus for laboratory animals according to the present invention, is not limited to the aforementioned example.

Figure 4:
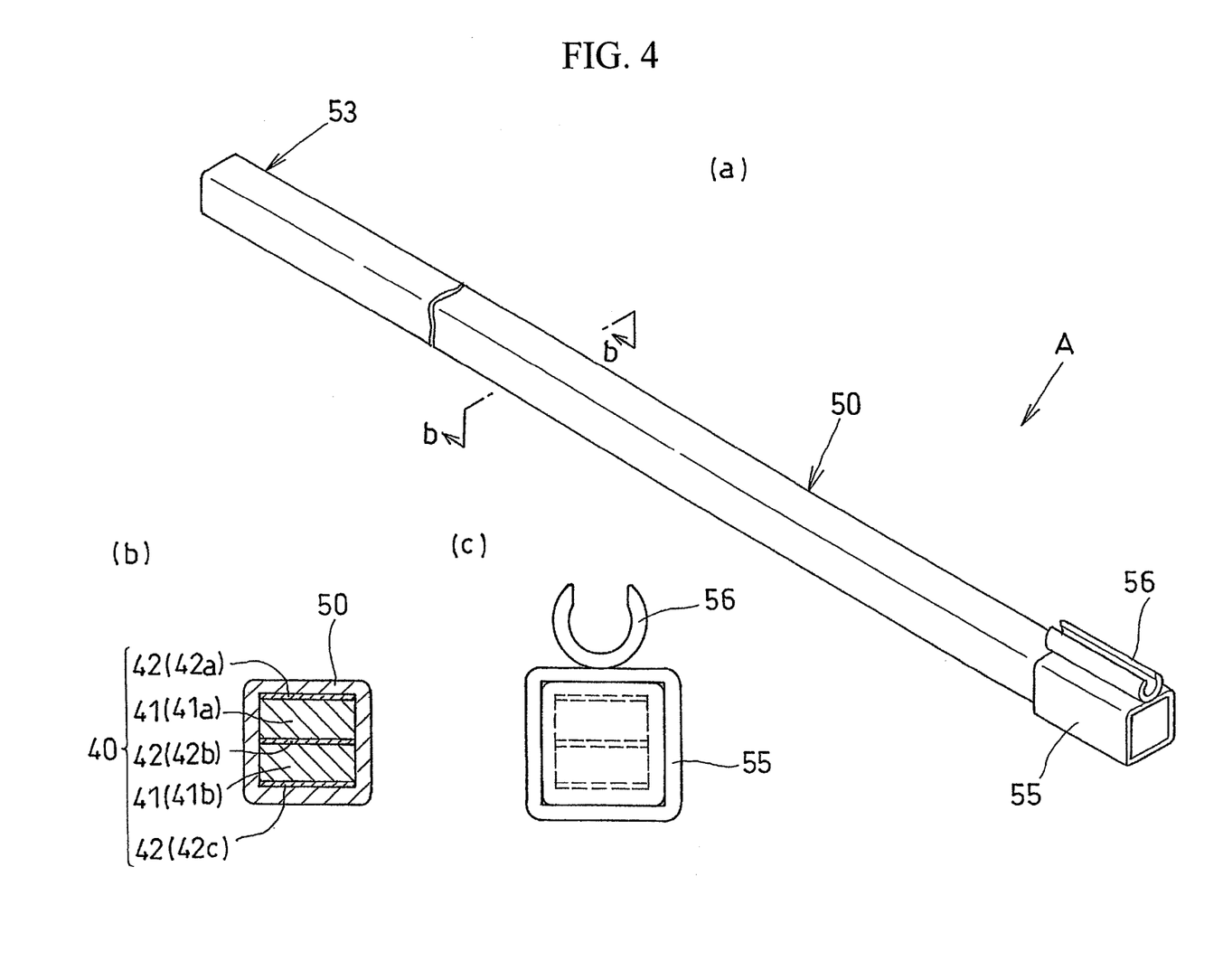
Figure 5:
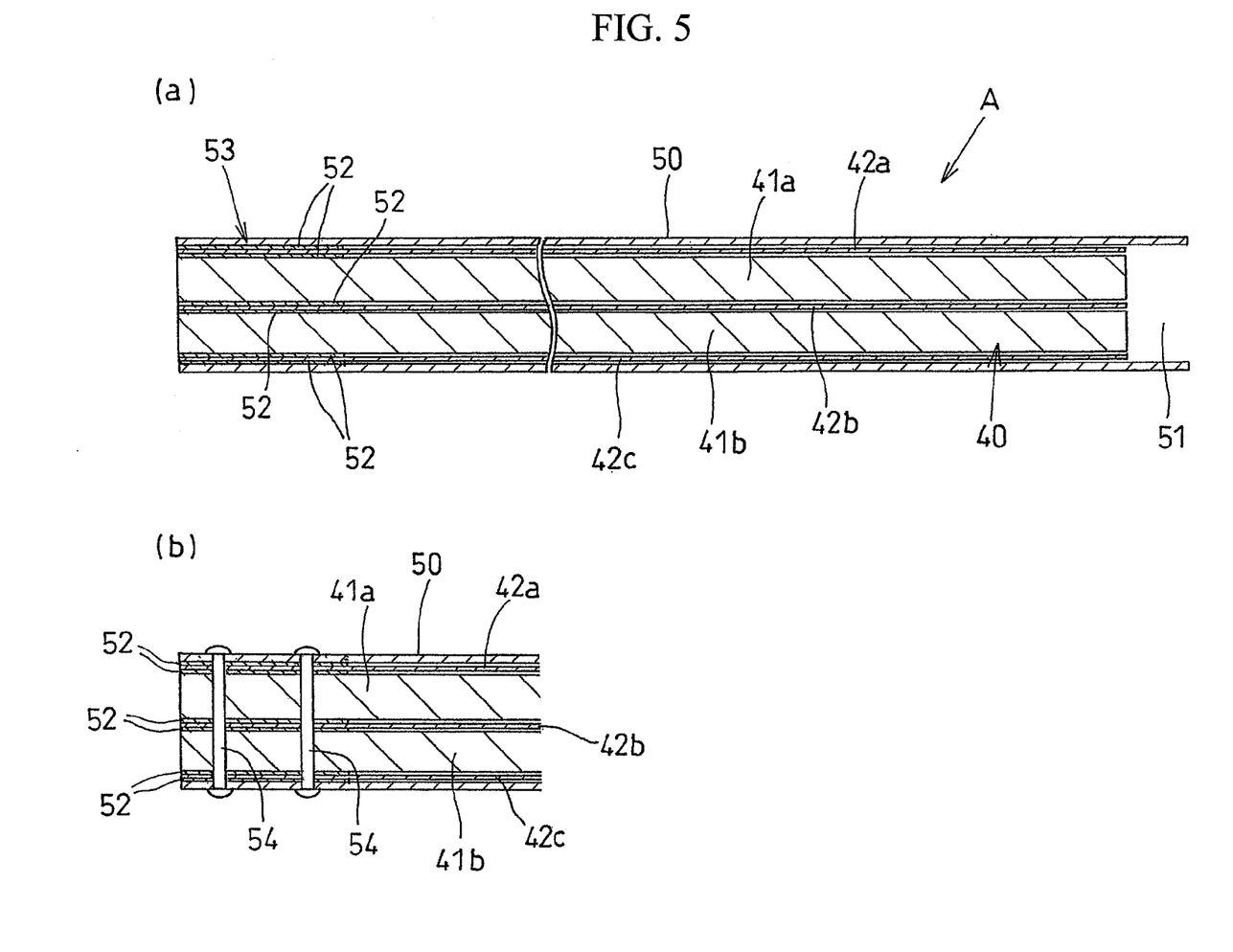
FIG. 5 is a schematic view for describing a layer structure of the flexible arm shown in FIG. 4.
Figure 6:
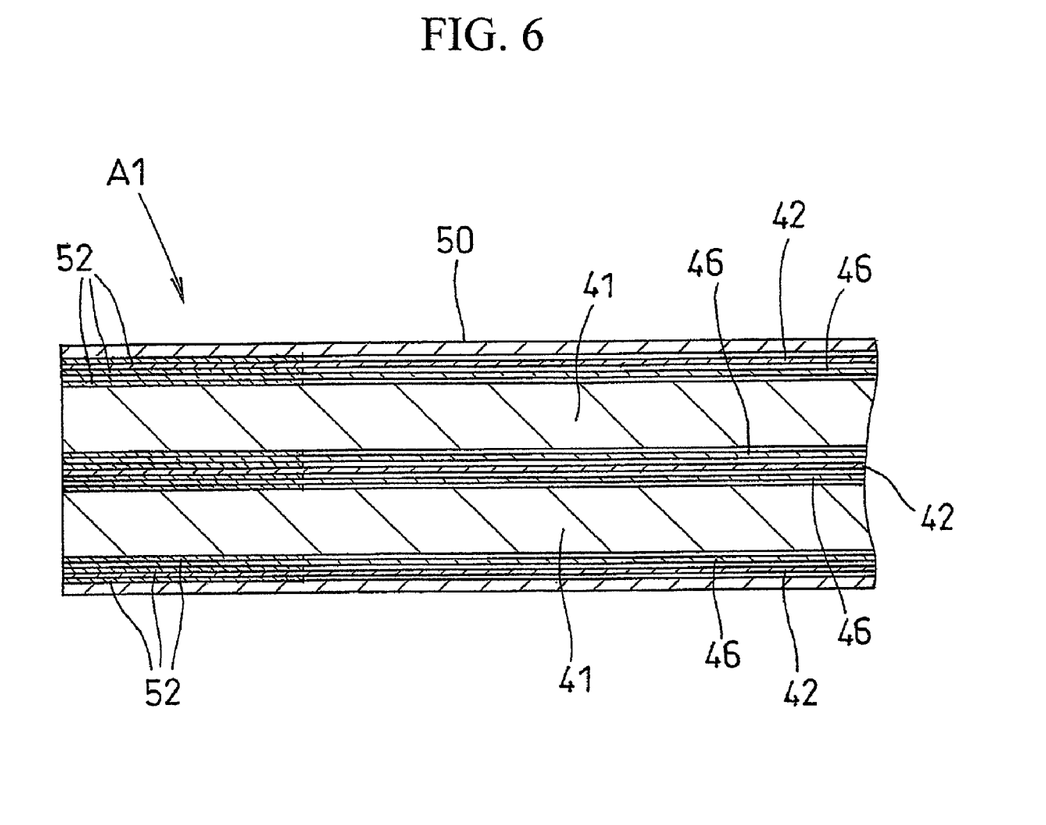
FIG. 6 is a diagram illustrating a laminated structure of a laminated body in another structure of a flexible arm.

As described above, in the automatic milking apparatus for laboratory animals according to the present invention, the teat cup 20 is supported by the free end of the flexible arm A unique to the present invention, which is shown in FIGS. 4 to 6, and the other end of the flexible arm A is fixed to the milk collecting container stand B that functions as a base. This configuration will be described below.

In this example, the milk collecting container stand B has a cylindrical shape, and is formed of a transparent material such as transparent acrylic resin in its entirety. At the center of the milk collecting container stand B, a vertical hole 2 having a size enough to stably support the transparent milk collecting container 10 is formed in a predetermined depth, and the inner surface of the vertical hole 2 is provided with a scale 3 for measuring the amount of milk in the milk collecting container 10.

Since the milk collecting container stand B is in a cylindrical shape and transparent, it can functions as a magnifying glass, and when the milk collecting container 10 is observed from the side through the milk collecting container stand B, the content (milked amount) and condition in the milk collecting container 10 can be measured and observed in a magnification by means of the lens effect.

FIGS. 4 to 6 show the flexible arm A. FIG. 4 is a perspective view of the entire flexible arm, FIG. 4b is a cross-sectional view taken along line b-b of FIG. 4a, and FIG. 4c is a front view. FIG. 5 is a schematic diagram for describing a layer structure for the flexible arm A shown in FIG. 4, and FIG. 6 is a schematic diagram illustrating another layer structure for the flexible arm.

The flexible arm A basically includes a long laminated body 40 and a coating member 50 coating the laminated body 40 from the outside. The long laminated body 40 includes long members 41 made of a material that is flexible and after being flexed, can maintain the shape, e.g., aluminum plates or lead plates, and steel plate members 42, which is a spring steel, arranged along the long members 41. In the shown example, the long laminated body 40 has a five-layer structure consisting of a steel plate member 42a, a long member 41a, a steel plate member 42b, a long member 41b and a steel plate member 42c, which are laminated in such a manner that they are in contact with one another but may slip relative to one another when they are flexed in their entirety. In the example, the cross-sectional dimensions of the long members 41 are both 2 mm×5 mm and the cross-sectional dimensions of the steel plate members 42 are all 0.2 mm×5 mm, thought the cross-sectional dimensions are not limited to the above example.

The coating member 50 is made of a resin material such as silicon resin, has a rectangular shape in cross section, and has a space 51 inside, which the laminated body 40 can be inserted with no gap formed.

As schematically shown in FIG. 5a, the laminated body 40 is inserted to the inner space 51 of the coating member 50 to form the flexible arm A, and industrial adhesives 52 are injected into one end of the flexible arm A (the left end portion in the Figure), and as a result of the adhesives 52 being cured, a secured part 53 in which long members 41, the steel plate members 42 and the coating member 50 are integrally secured so that no relative movement occurs between each of them. At the part other than the secured part 53, as described above, the long members 41, the steel plate members 42 and the coating member 50 can slip relative to one another through their mutual contact surfaces, and change in the longitudinal direction of the long members 41 and the steel plate members 42, which is caused when the flexible arm A is flexed, is absorbed by the free end, which is the other end (the right end portion in the Figure). In FIG. 5a, for the convenience of illustration, the other region except the secured part 52 is drawn as if it has a gap between the respective members, but in an actual product, the members are pressure-bonded by the coating member 50 so that no gaps are formed between the respective members.

When this flexible arm A is curved so that it forms into an arc with a certain radius, for example, the respective members in the other part except the secured part 53 are displaced in the longitudinal direction, and such displacements cause slippage between the respective members in the other part except the secured part 53, which are absorbed by the free end, and as schematically shown in FIG. 3, steps appear at the tip of the laminated body 40 at the free end.

FIG. 5b is a schematic diagram illustrating another structure of the secured part 53 of the flexible arm A, and here, locking pins 54 are inserted into the secured part 53, and the ends of the locking pins 54 are squashed, whereby the integration of the respective members are further strengthened.

In an experiment, the present inventor has confirmed that when the above-described flexible arm A is used, the free end can be moved with freedom, i.e., forward, backward, rightward or leftward or at an angle, etc., and after being moved in such a manner to be positioned at a predetermined position, the free end remains at the position for a long period of time even though the hands being released from it. When a similar experiment was conduced using a flexible arm with no adhesives 52 injected to one end thereof for comparison, the degree of freedom for the free end's movement was good, but upon the hands being released from the free end after the free end being positioned at a predetermined position, the free end was considerably moved. It can be presumed that this is because there was no secured part 53, resulting in both ends of the laminated body 40 being free ends.

Although it is not essential, in the example, a milk tube holder 55, which is preferably made of a resin material, is attached to the free end of the flexible arm A. The milk tube holder 55 has a U-shaped clip 56, and when milking, as shown in FIG. 3, the first milk tube 12 is slidably inserted into the U-shaped clip 56. Also, the secured end 53 of the flexible arm A is fixed to the milk collecting container stand B via suitable means.

When milking, as shown in FIG. 3, the transparent milk collecting container 10 is inserted into the vertical hole 2 formed in the milk collecting container stand B. The milk collecting container 10 is capped with a sealing cap 11, and the other end of the first milk tube 12 fitted with the teat cup 20 and one end of the second milk tube 13 are inserted into the sealing cap 11 in such a manner that they are in fluid communication with the milk collecting container 10. Furthermore, a part of the first milk tube 12 near the teat cup 20 is slidably inserted into the U-shaped clip 56 of the milk tube holder 55 attached to the free end of the flexible arm A.

The laboratory animal to be milked (not shown) is placed near the milk collecting container stand B, and the experimenter moves the teat cup 20 to the position of a teat of the laboratory animal to fit it onto the teat. The teat cup 20 is attached to the free end of the flexible arm A unique to the present invention, and moves smoothly, and the teat cup 20 fitted on the teat stably remains at that position even though the experimenter releases his/her hands from it. Under that condition, an automatic milking apparatus for laboratory animals is activated in such a manner as described with reference to FIG. 1 to start milking from the laboratory animal.

The expressed breast milk is collected in the transparent milk collecting container 10. Since the milk collecting container stand B, as described above, functions as a magnifying glass, the experimenter can definitely measure and observe the content (milked amount) and condition of the milk collecting container 10 through the milking process. The apparatus operates fully automatically until the completion of collection of the required amount of milk. Consequently, during milking, the experimenter can have his/her hands free and leave the milking apparatus, and thus can perform work such as introduction of inhalation anesthesia to the laboratory animal without interrupting milking performed by the milking apparatus.

In the apparatus, the first milk tube 12 with its tip fitted with the teat cup 20 is slidably attached to the U-shaped clip 56 of the milk tube holder 55, which is attached to the flexible arm A, and accordingly, the distance between the laboratory animal and the teat cup 20 can easily be fine adjusted as necessary.

For the flexible arm A, it is possible to form a flexible arm A similar to the aforementioned one using long members 41 each formed by depositing a polyethylene resin sheet stretched in a single axis direction (product name "Forte" manufactured by Sekisui Chemical Co., Ltd.) in such a manner that it has a cross-sectional shape that is substantially the same as that of the aforementioned flexible arm A and configure a milking apparatus that is the same as the aforementioned one, using it. In that case, since the members are of a single axis stretched material, their rightward and leftward movement is inferior to that of a lead plate, but its upward, downward, forward and backward movement is substantially the same as that of a lead plate, and accordingly, the teat cup 20 can be positioned in a desired position. However, when releasing the hands from it after the positioning to the predetermined position, the teat cup 20 is slightly displaced. However, such displacement is not such as hindering milking from the laboratory animal, and is sufficient for practical use.

FIG. 6 shows a laminated structure of a laminated body 40 in another structure of a flexible arm A1, which is different from the aforementioned flexible arm A in that resin sheets 46 of e.g., polyethylene, are provided between the layers of long members 41, which are aluminum plates or lead plates, and steel plate members 42. The provision of the resin sheets 46 between the layers as described above provides good slippage between the layers and easy positioning. However, as described above, if the slippage between the layers is overly good, the resilience of the steel plate members 42 prevails and displacement may easily occur after positioning. In such a case, it is not preferable to provide the resin sheets 46.

EXPERIMENTAL EXAMPLE

An experiment was conducted to verify that a flexible arm used in an automatic milking apparatus for laboratory animals according to the present invention can maintain a substantially same shape over a long period of time. For the experiment, two types of five-layer flexible arm A shown in FIGS. 4 and 5 were prepared by changing the kind of the long members 41 only. The entire length of the flexible arm A was 270 mm, each steel plate member 42 was a spring steel having cross-sectional dimensions of 0.2 mm in thickness and 5 mm in width, and the coating member 50, which is made of silicon resin, has inside dimensions of 5.2 mm×5.2 mm and a wall thickness of 1 mm. One end of the flexible arm A was fixed by the industrial adhesives 52. For the long members 41, one flexible arm Aa used an aluminum plate having cross-sectional dimensions of 1.5 mm in thickness and 5 mm in width, the other flexible arm Ab used a lead plate having cross-sectional dimensions of 1.5 mm in thickness and 5 mm in width.

Both ends of each of the flexible arms Aa and Ab were held by hands and were curved into a U shape until the ends are made into contact with each other. The distance (mm) between both ends was measured serially after placing each of flexible arms Aa and Ab on copier paper provided over a horizontal surface and releasing the hands from it to release it from the load. The test was conduced three times for each of them. The results are shown in Table 1.

TABLE 1

|  | Immediately after | 1 minute | 5 minutes | 10 minutes | 15 minutes | 20 minutes | 25 minutes | 30 minutes | 40 minutes | 50 minutes | 60 minutes |
|---|---|---|---|---|---|---|---|---|---|---|---|
| Aluminum plate (Aa) | 32 | 32 | 32 |  |  |  |  | 32 |  |  | 32 |
|  | 31 | 31 | 31 |  |  |  |  | 31 |  |  | 31 |
|  | 30 | 30 | 30 |  |  |  |  | 30 |  |  | 30 |
| Lead plate (Ab) |  | 57 | 59 | 61 | 62 | 64 | 65 | 66 | 67 | 67 | 67 |
|  |  | 58 | 66 | 68 | 70 | 71 | 72 | 73 | 73 | 73 | 73 |
|  |  | 62 | 66 | 69 | 70 | 71 | 71 | 72 | 73 | 73 | 73 |

[Evaluation]

The resiliences of an aluminum plate and a lead plate (long member 41) are small compared to that of a steel plate (steel plate member 42), which is a spring plate, and the resiliences of an aluminum plate and a lead plate are different from each other. Accordingly, it is shown that: the distance between both ends one minute after the release from the load is different between the flexible arm Aa (aluminum plate) and the flexible arm Ab (lead plate); and it becomes substantially unchanged after a lapse of a certain period of time for both of them.

In other words, in the flexible arm Aa (aluminum plate), the distance immediately after the release from the load is maintained after a lapse of 60 minutes, and in the flexible arm Ab (lead plate), the distance varies for around 20 minutes after the release from the load but no variation can be observed thereafter.

The distance immediately after the release from the load was affected by what is called springback, and resulted from the flexible arm having been curved to a degree that is more than that applied in ordinary actual use. In either flexible arm, the state in which the distance has been unchanged was maintained thereafter, which shows that a flexible arm that can easily be handled and limit displacement of the free end of the arm after release from a load can be obtained by selecting suitable materials and dimensions depending on the load. Such flexible arm is highly effective as means for holding a teat cup for laboratory animals in an automatic milking apparatus for laboratory animals.

The invention claimed is:

1. An automatic milking apparatus for laboratory animals in which an end of a milk tube having another end connected to a teat cup for laboratory animals to be fitted onto a udder of a laboratory animal is connected to a negative-pressure generating source via a milk collecting container to collect milk from the laboratory animal into the milk collecting container through suction pulsation provided by the negative-pressure generating source, characterized in that
the end of the milk tube connected to the teat cup for laboratory animals is supported by a free end of a flexible arm having a rectangular shape in cross section, with one end fixed to a base, the flexible arm including a laminated body that includes a long member having a rectangular shape in cross section, formed of a material that is flexible and after being flexed, can maintain the shape and a steel plate member having a rectangular shape in cross section, arranged along the long member, the laminated body being coated by a coating member, the members being in contact with each other in such a manner that they slip relative to each other upon being flexed in their entirety, the flexible arm including a secured part formed at the one end, the secured part preventing relative movement of the respective members.

2. The automatic milking apparatus for laboratory animals according to claim 1, characterized in that: a milk tube holder that can slidably support the milk tube is attached to the free end of the flexible arm; and the milk tube is supported by the free end of the flexible arm via the milk tube holder.

3. The automatic milking apparatus for laboratory animals according to claim 2, characterized in that the long member in the flexible arm is any of an aluminum plate, a lead plate or a resin plate.

4. The automatic milking apparatus for laboratory animals according to claim 3, characterized in that the flexible arm includes a structure in which a resin sheet is provided between the layers of the long member and the steel plate member.

5. The automatic milking apparatus for laboratory animals according to claim 2, characterized in that the flexible arm includes a structure in which a resin sheet is provided between the layers of the long member and the steel plate member.

6. The automatic milking apparatus for laboratory animals according to claim 1, characterized in that the long member in the flexible arm is any of an aluminum plate, a lead plate or a resin plate.

7. The automatic milking apparatus for laboratory animals according to claim 6, characterized in that the flexible arm includes a structure in which a resin sheet is provided between the layers of the long member and the steel plate member.

8. The automatic milking apparatus for laboratory animals according to claim 1, characterized in that the flexible arm includes a structure in which a resin sheet is provided between the layers of the long member and the steel plate member.

9. An automatic milking apparatus for laboratory animals in which an end of a milk tube having another end connected to a teat cup for laboratory animals to be fitted onto a udder of a laboratory animal is connected to a negative-pressure generating source via a milk collecting container to collect milk from the laboratory animal into the milk collecting container through suction pulsation provided by the negative-pressure generating source, characterized in that
the end of the milk tube connected to the teat cup for laboratory animals is supported by a free end of a flexible arm with one end fixed to a base, the flexible arm including a laminated body that includes a long member formed of a material that is flexible and after being flexed, can maintain the shape and a steel plate member arranged along the long member, the laminated body being coated by a coating member, the members being in contact with each other in such a manner that they slip relative to each other upon being flexed in their entirety, the flexible arm including a secured part formed at the one end, the secured part preventing relative movement of the respective members,
characterized in that: the automatic milking apparatus for laboratory animals further comprises a milk collecting container stand that is a transparent cylindrical body; a vertical hole to hold the milk collecting container is formed in the milk collecting container stand; a scale for measuring an amount of milk in the milk collecting container is provided on an inner surface of the vertical hole; and the secured part of the flexible arm is fixed to the milk collecting container stand.

10. The automatic milking apparatus for laboratory animals according to claim 9, characterized in that the long member in the flexible arm is any of an aluminum plate, a lead plate or a resin plate.

11. The automatic milking apparatus for laboratory animals according to claim 10, characterized in that the flexible arm includes a structure in which a resin sheet is provided between the layers of the long member and the steel plate member.

12. The automatic milking apparatus for laboratory animals according to claim 9, characterized in that the flexible arm includes a structure in which a resin sheet is provided between the layers of the long member and the steel plate member.

13. An automatic milking apparatus for laboratory animals in which an end of a milk tube having another end connected to a teat cup for laboratory animals to be fitted onto a udder of a laboratory animal is connected to a negative-pressure generating source via a milk collecting container to collect milk from the laboratory animal into the milk collecting container through suction pulsation provided by the negative-pressure generating source, characterized in that the end of the milk tube connected to the teat cup for laboratory animals is supported by a free end of a flexible arm with one end fixed to a base, the flexible arm including a laminated body that includes a long member formed of a material that is flexible and after being flexed, can maintain the shape and a steel plate member arranged along the long member, the laminated body being coated by a coating member, the members being in contact with each other in such a manner that they slip relative to each other upon being flexed in their entirety, the flexible arm including a secured part formed at the one end, the secured part preventing relative movement of the respective members, wherein a milk tube holder that can slidably support the milk tube is attached to the free end of the flexible arm; and the milk tube is supported by the free end of the flexible arm via the milk tube holder, characterized in that: the automatic milking apparatus for laboratory animals further comprises a milk collecting container stand that is a transparent cylindrical body; a vertical hole to hold the milk collecting container is formed in the milk collecting container stand; a scale for measuring an amount of milk in the milk collecting container is provided on an inner surface of the vertical hole; and the secured part of the flexible arm is fixed to the milk collecting container stand.

14. The automatic milking apparatus for laboratory animals according to claim 13, characterized in that the long member in the flexible arm is any of an aluminum plate, a lead plate or a resin plate.

15. The automatic milking apparatus for laboratory animals according to claim 14, characterized in that the flexible arm includes a structure in which a resin sheet is provided between the layers of the long member and the steel plate member.

16. The automatic milking apparatus for laboratory animals according to claim 13, characterized in that the flexible arm includes a structure in which a resin sheet is provided between the layers of the long member and the steel plate member.

* * * * *